(12) United States Patent
Malin (10) Patent No.: US 9,709,314 B2
(45) Date of Patent: Jul. 18, 2017

(54) LOW-TEMPERATURE STORAGE DEVICE WITH ROTATING LOCK CHAMBER

(71) Applicant: LICONIC AG, Mauren (LI)

(72) Inventor: Cosmas G. Malin, Mauren (LI)

(73) Assignee: LICONIC AG, Mauren (LI)

( * ) Notice: Subject to any disclaimer, the term of this patent is extended or adjusted under 35 U.S.C. 154(b) by 127 days.

(21) Appl. No.: 14/860,011

(22) Filed: Sep. 21, 2015

(65) Prior Publication Data
US 2016/0084564 A1    Mar. 24, 2016

(30) Foreign Application Priority Data
Sep. 22, 2014 (CH) ........................ 1430/14

(51) Int. Cl.
 F25D 13/06 (2006.01)
 F25D 25/04 (2006.01)
 B01L 7/00 (2006.01)

(52) U.S. Cl.
 CPC ............... *F25D 13/06* (2013.01); *B01L 7/50* (2013.01); *F25D 25/04* (2013.01); *B01L 2200/025* (2013.01); *B01L 2200/0689* (2013.01); *B01L 2300/0841* (2013.01)

(58) Field of Classification Search
 CPC ........ F25D 13/06; F25D 25/04; F25D 13/062; F25D 13/065; F25D 25/028; F25D 31/00; F25D 31/003; B01L 7/50; B01L 2300/0841; B01L 2200/025; B01L 2200/0689; B01L 7/00; B01L 7/525; B01L 7/5255; B01L 9/523
 USPC ................................... 62/266, 381
 See application file for complete search history.

(56) References Cited

U.S. PATENT DOCUMENTS

| 3,272,579 | A | | 9/1966 | Leonard |
| 3,782,133 | A | | 1/1974 | Desperier et al. |
| 4,250,266 | A | | 2/1981 | Wade |
| 4,907,889 | A | | 3/1990 | Simone |
| 4,981,409 | A | | 3/1991 | Hirose et al. |
| 5,224,415 | A | * | 7/1993 | McFadden .......... A47J 37/1228 221/150 HC |
| 5,233,844 | A | | 8/1993 | Knippscheer et al. |
| 5,345,395 | A | | 9/1994 | Griner |
| 5,365,980 | A | | 11/1994 | Deberardinis |
| 5,449,229 | A | | 9/1995 | Aschenbrenner et al. |
| 5,735,587 | A | | 4/1998 | Malin et al. |
| 5,921,102 | A | | 7/1999 | Vago |

(Continued)

FOREIGN PATENT DOCUMENTS

DE   2 254 218    11/1972
EP   0 725 133    8/1996

(Continued)

OTHER PUBLICATIONS

European Search Report conducted in counterpart Europe Appln. No. 15 002 719.1-1605 (Mar. 14, 2016).

*Primary Examiner* — Mohammad M Ali
(74) *Attorney, Agent, or Firm* — Greenblum & Bernstein, P.L.C.

(57) ABSTRACT

The storage device comprises a storage chamber for storing objects at e.g. −80° C., a transfer chamber for intermediate object storage at e.g. −20° C. and a transport device arranged between them. The transport device comprises a pivotal and vertically displaceable carriage and is arranged in a rotatable lock chamber.

23 Claims, 7 Drawing Sheets

(56) References Cited

U.S. PATENT DOCUMENTS

| | | | |
|---|---|---|---|
| 6,059,507 A | 5/2000 | Adams | |
| 6,068,393 A | 5/2000 | Hutchins et al. | |
| 6,129,428 A | 10/2000 | Helwig et al. | |
| 6,357,983 B1 | 3/2002 | Junca | |
| 6,478,524 B1 | 11/2002 | Malin | |
| 6,568,770 B2 | 5/2003 | Gonska et al. | |
| 6,581,395 B2* | 6/2003 | Felder | F25D 25/00 62/177 |
| 6,673,595 B2 | 1/2004 | Barbera-Guillem | |
| 6,694,767 B2 | 2/2004 | Junca et al. | |
| 7,544,329 B2 | 6/2009 | Malin | |
| 2001/0043031 A1 | 11/2001 | Gonska et al. | |
| 2003/0196446 A1* | 10/2003 | Sands | F25D 25/04 62/378 |
| 2003/0233842 A1 | 12/2003 | Junca et al. | |
| 2004/0115101 A1 | 6/2004 | Malin | |
| 2004/0213651 A1 | 10/2004 | Malin | |
| 2006/0150659 A1* | 7/2006 | Sidor | F25D 13/06 62/378 |
| 2006/0156753 A1 | 7/2006 | Fuhr et al. | |
| 2008/0231152 A1 | 9/2008 | Malin | |
| 2009/0175763 A1 | 7/2009 | Malin | |
| 2009/0188272 A1* | 7/2009 | Cloutier | F25D 13/04 62/378 |
| 2010/0183408 A1* | 7/2010 | Malin | F25D 16/00 414/222.01 |
| 2010/0275636 A1 | 11/2010 | Yoshimura et al. | |
| 2011/0183411 A1* | 7/2011 | Nichols | A61L 2/06 435/303.1 |
| 2012/0060520 A1* | 3/2012 | Collins | A01N 1/0236 62/62 |
| 2012/0134898 A1 | 5/2012 | Malin | |
| 2014/0190977 A1 | 7/2014 | Malin | |

FOREIGN PATENT DOCUMENTS

| | | |
|---|---|---|
| JP | 2005-143873 | 6/2005 |
| WO | 98/05753 | 2/1998 |

\* cited by examiner

LOW-TEMPERATURE STORAGE DEVICE WITH ROTATING LOCK CHAMBER

CROSS REFERENCES TO RELATED APPLICATIONS

This application claims the priority of Swiss patent application 1430/14, filed Sep. 22, 2014, the disclosure of which is incorporated herein by reference in its entirety.

TECHNICAL FIELD

The invention relates to a low-temperature storage device for storing a plurality of objects at a temperature of less than 0° C., in particular below −20° C., typically at approximately −80° C.

BACKGROUND ART

A device of this type is described in US 2003/0233842.

Storage devices of this type require sophisticated thermal and atmospheric insulation. In particular, warm air with comparatively high water content should be prevented from entering the storage chamber in order to avoid ice formation within the chamber.

This is particularly true for storage devices adapted to store objects at temperatures below −20° C., in particular at approximately −80° C.

On the other hand, many applications of such storage devices, in particular as used in laboratory automation, require the objects in the storage chamber to be accessible by means of an automated transport device, such as a robot.

DISCLOSURE OF THE INVENTION

The problem to be solved by the present invention is therefore to provide a storage device of this type that is efficiently accessible by means of an automatic transport device and that provides a good insulation of the storage chamber.

This problem is solved by the low-temperature storage-device of claim 1.

Accordingly, the low-temperature storage device comprises the following:

A storage chamber for receiving the objects. This storage chamber typically contains a plurality of storage locations, e.g. formed by shelves or ledges in storage cassettes, for receiving the objects.

A refrigerator device adapted and structured to cool the storage chamber to a storage temperature below 0° C., in particular below −20° C. The refrigerator device can e.g. comprise one or more heat pumps, and the storage temperature is advantageously between −90° C. and −60° C.

An insulating wall enclosing the storage chamber. This wall provides thermal insulation. Also, it is advantageously gas-tight in order to prevent humidity from entering the storage chamber. It can comprise one or more closeable openings.

A transfer location arranged outside said storage chamber. This is a designated location for intermediately receiving objects that leave the storage chamber or that are to be moved into the storage chamber.

A lock chamber arranged in said insulating wall, wherein said lock chamber comprises a cylindrical housing and an opening arranged in said cylindrical housing, and wherein said lock chamber is rotatable about a first axis for selectively orienting said opening towards said storage chamber or said transfer location. The objects can pass this lock chamber on their way between the storage chamber and the transfer location. The lock chamber prevents a free gas exchange between the storage chamber and its surroundings.

An automatic transport device arranged in said lock chamber, wherein said transport device comprises a) a carriage pivotal—relatively to (i.e. in relation to) said lock chamber—about a second axis and/or displaceable—relatively to said lock chamber—along the second axis, wherein said second axis is parallel to said first axis, b) a manipulator arranged on said carriage and extendible from a retracted position in a direction perpendicular to said second axis into an extended position, and wherein said transport device is adapted to transport objects between said storage chamber and said transfer location by means of said manipulator.

The transport device can be used to manipulate the objects. By pivoting its carriage about the second axis, it can be aligned along a desired direction where an object is to be received or deposited. By said carriage being displaceable along said second axis, it can be adjusted to a desired height where an object is to be received or deposited.

By providing the pivotal and/or displaceable carriage in addition to having a rotatable lock chamber, it becomes possible to quickly and easily adjust the position of manipulator. Due to its higher weight and potentially higher friction, such movements could not be easily carried out by the lock chamber alone.

Advantageously, the transport device is pivotal about as well as displaceable along the second axis.

Advantageously, the device further comprises, at said transfer location, a plurality of transfer storage locations, with each transfer storage location adapted to receive one of said objects. In this case, the carriage of the transport device can be pivotal about and/or displaceable along said second axis to be aligned with each of said transfer storage locations. In this case, several transfer storage locations can be handled by the transport device.

The device can also comprise an item picker at said transfer location. This item picker is equipped with an item picker location for receiving an object and a picker device for removing an individual item from a plurality of items in said object at said picker location or for adding an individual item to a plurality of items in said object at said picker location.

In this case, the carriage of the transport device is pivotal about and/or displaceable along said second axis to be aligned with said picker location. Hence, the transport device can also be adapted to exchange objects with such an item picker.

Advantageously, the transfer storage locations are arranged above or below said item picker in order to provide a compact arrangement of parts in the transfer location.

In yet another embodiment, the device can further comprise a transfer chamber receiving said transfer location. In this case, the refrigerator device is adapted and structured to cool said transfer chamber to a transfer temperature below 0° C., but above the storage temperature. By providing such a transfer chamber at a low temperature, the flux of humidity into the storage chamber can be reduced further. However, the temperature of the transfer chamber is above the one of the storage chamber, which allows to place cold-sensitive components therein and/or allows better access for users.

The transfer chamber can further receive a transfer device structured and adapted to transfer objects between a first and second object location. The carriage of the transport device is pivotal about and/or displaceable along the second axis to be aligned with said first object location and to reach an object in said first object location. The second object location is at an opening of a housing of the low-temperature storage device. This provides a path for moving objects between the storage chamber and the outside of the low-temperature storage device.

The present invention is advantageously used for storing laboratory objects, in particular microplates, such as multi-well plates or sample tube holders, having the standardized SBS footprint of 127.75×85.48 mm.

Other advantageous embodiments are listed in the dependent claims as well as in the description below.

BRIEF DESCRIPTION OF THE DRAWINGS

The invention will be better understood and objects other than those set forth above will become apparent from the following detailed description thereof. Such description makes reference to the annexed drawings, wherein.

MODES FOR CARRYING OUT THE INVENTION

Definitions

A "low-temperature storage device" is a storage device adapted to store objects at temperatures below 0° C., in particular below −20° C., advantageously between −90° C. and −60° C.

An "automated" transport device is a transport device structured and adapted to be controlled and operated electronically by means of a control unit performing autonomous operations.

Figure 1:
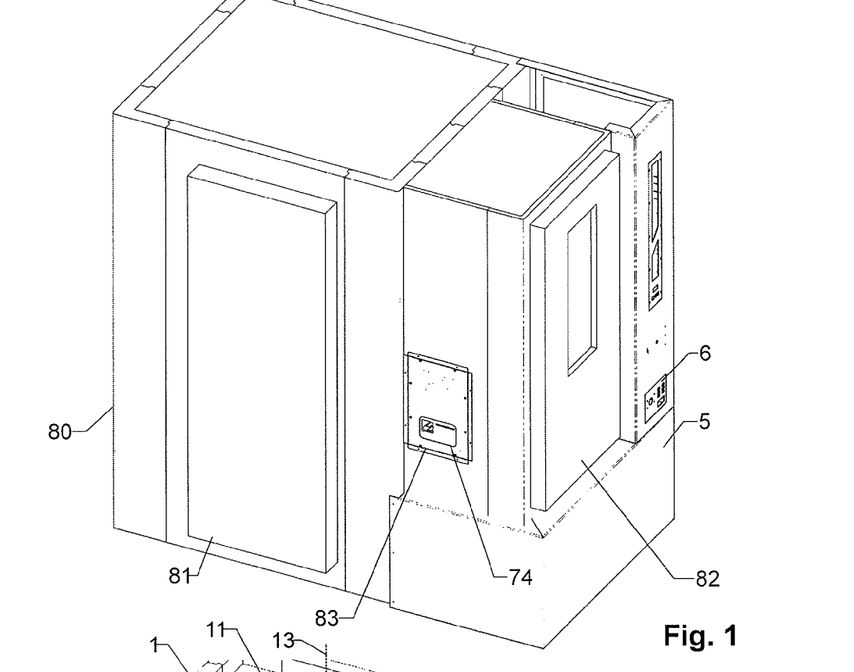
FIG. 1 shows a view of a low-temperature device.
Figure 2:
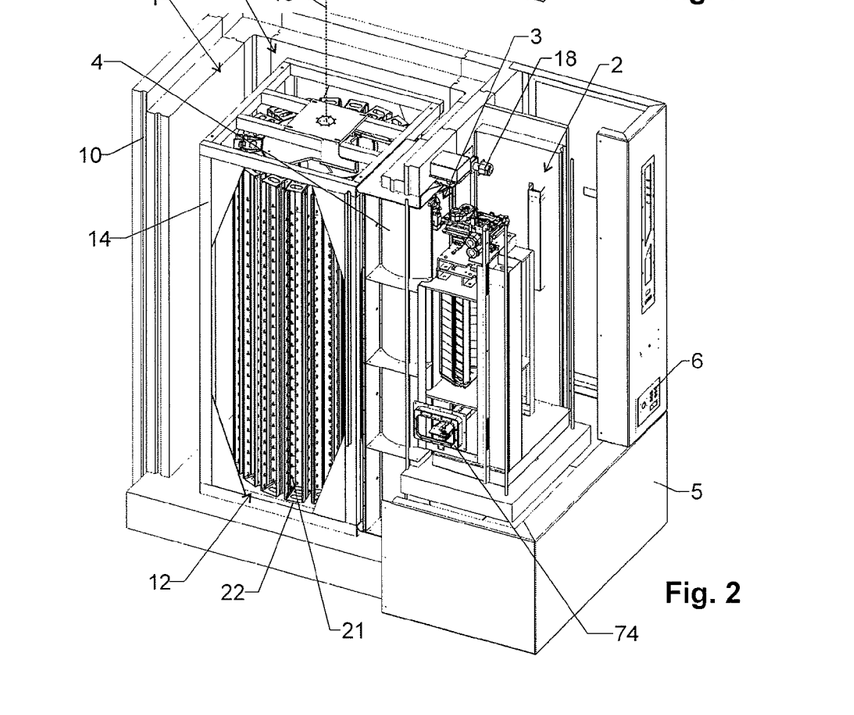
FIG. 2 shows the device of FIG. 1 with partially removed walls.
Figure 3:
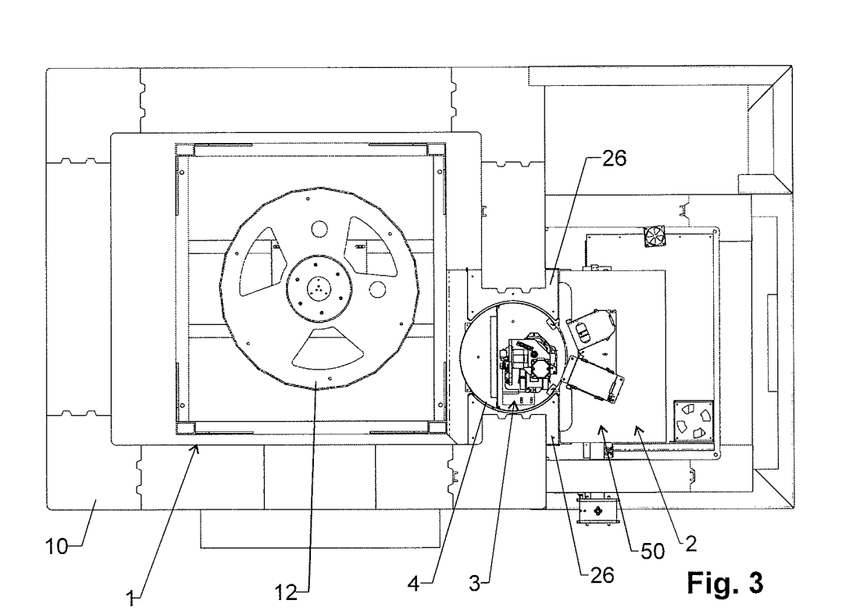
FIG. 3 shows a top view of the device with the top walls removed and the storage cassettes on the carousel not shown.

Overview:

FIGS. 1-3 show a low-temperature storage device for storing laboratory objects at low temperatures. It comprises a storage chamber 1 for storing the objects at temperatures e.g. between −60 and −90° C. It further comprises a transfer chamber 2 for temporarily receiving the objects at e.g. −20° C. A transport device 3 in a lock chamber 4 is used for automatically moving objects between storage chamber 1 and transfer chamber 2. A refrigerator device 5 is provided for cooling storage chamber 1 and transfer chamber 2. A control unit 6 controls the various components of the storage device.

These components are described in more detail in the following.

Storage Chamber:

Storage chamber 1 comprises insulating walls 10 surrounding an inner space 11 having a substantially quadratic footprint. Inner space 11 receives a storage carousel 12 rotatable about a vertical carousel axis 13 (the "third axis" in the context of the claims).

Figure 11:
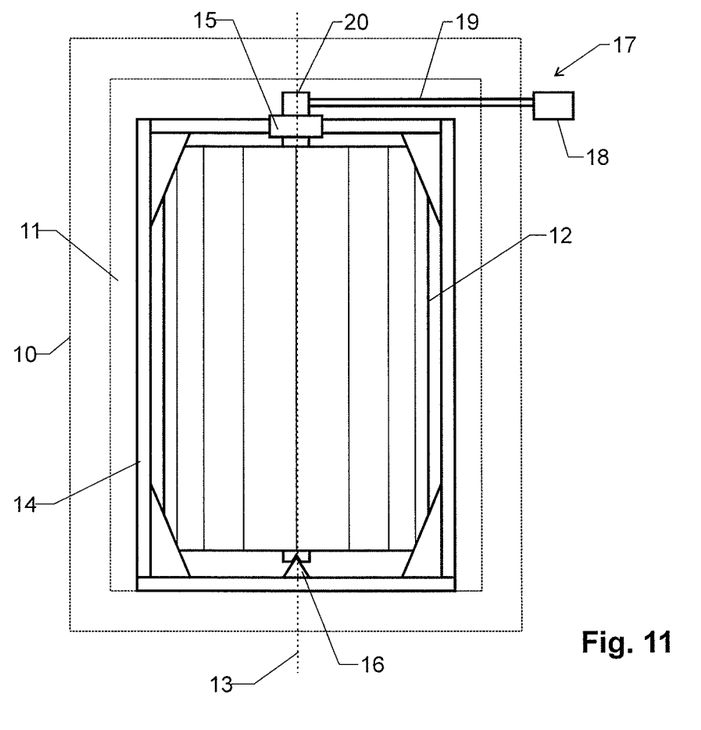
FIG. 11 shows a schematic view of the suspension of the carousel and FIG. 12 shows a schematic diagram of the components of the refrigerator device.

Carousel 12 is arranged in suspended fashion in a frame 14. As schematically shown in FIG. 11, a rotational bearing 15 mounted to frame 14 and located at the top or above carousel 12 receives the weight of carousel 12 (i.e. at least 90% of its weight). A substantially no-weight-carrying bearing 16 located at the bottom of the carousel is used for keeping carousel axis 13 in its vertical alignment. Suspending carousel 12 in this manner has the advantage that the weight-receiving bearing 15 is located at the warmest location of storage chamber 1.

A carousel drive 17 is provided for rotating carousel 12 about carousel axis 13. Carousel drive 17 comprises a carousel motor 18 (see FIGS. 2 and 11), which is arranged outside storage chamber 1 such that it is not exposed to extremely low temperatures. Carousel motor 18 drives a shaft 19, which extends into storage chamber 1 in order to rotate carousel 12.

Advantageously, carousel motor 18 is located in transfer chamber 2 in order to keep the temperature gradient over shaft 19 low.

In the embodiment shown, shaft 19 extends horizontally, i.e. perpendicularly to carousel axis 13, and it drives carousel 12 for rotation about carousel axis 13 by means of an angular gear 20. This design minimizes the height of the storage device.

Carousel 12 forms a plurality of carousel storage locations 21 (FIG. 2), each for receiving one of the objects to be stored. As can be seen from FIG. 2, the carousel storage locations 21 are formed by a plurality of storage cassettes 22 arranged side by side along the periphery of carousel 12. Each storage cassette 22 contains a plurality of the storage locations 21 arranged above each other.

Lock Chamber:

The design of lock chamber 4 is best seen in FIGS. 4-7.

Figure 7:
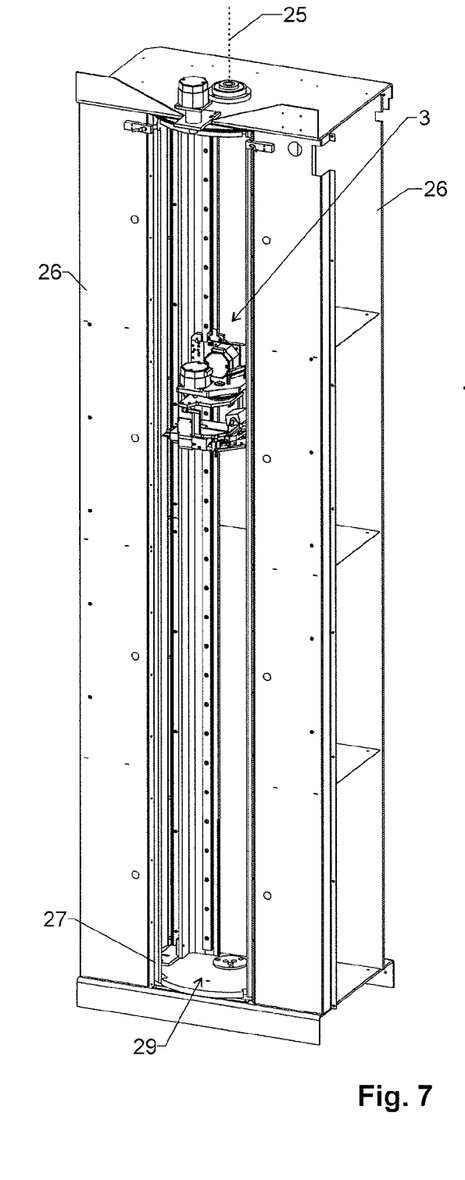
FIG. 7 shows the lock chamber with its surrounding frame.

Lock chamber 4 is basically arranged in insulating wall 10 of storage chamber 1. As shown in FIG. 7, it is rotatable about a vertical lock chamber axis 25 (the "first axis" in the context of the claims) and located within a stationary lock frame 26. A gas tight sealing is arranged between lock frame 26 and the basically cylindrical outer housing 27 of lock chamber 4 in order to prevent moisture from entering storage chamber 1.

An opening 29 is arranged in cylindrical housing 27. Opening 29 extends from the top of lock chamber 4 to its bottom and has uniform width along its whole height in order to allow the carriage of the transport device to operate at a wide range of vertical positions, as described below.

The interior of lock chamber 4 is divided along a plane 30 (FIG. 4) into two sections 31, 32. In the embodiment shown here, plane 30 coincides with a separating wall 33. Separating plane 30 extends parallel to opening 29. First section 31 of lock chamber 4 receives a thermal insulator 34, while second section 32 receives transport device 3.

Thermal insulator 34, which can e.g. be a vacuum insulator, has a maximum thickness at a location opposite opening 29. It reduces the thermal losses from lock chamber 1 through lock chamber 4. Advantageously, the maximum radial thickness ("radial" in respect to lock chamber axis 25) of thermal insulator 34 is at least 50% of the radius of cylindrical housing 27.

Transport Device:

Transport device 3 is, as mentioned, arranged within second section 32 of lock chamber 4. Its design can best be seen in FIGS. 4-8. Its purpose is to move objects between storage chamber 1 and transfer chamber 2.

Figure 8:
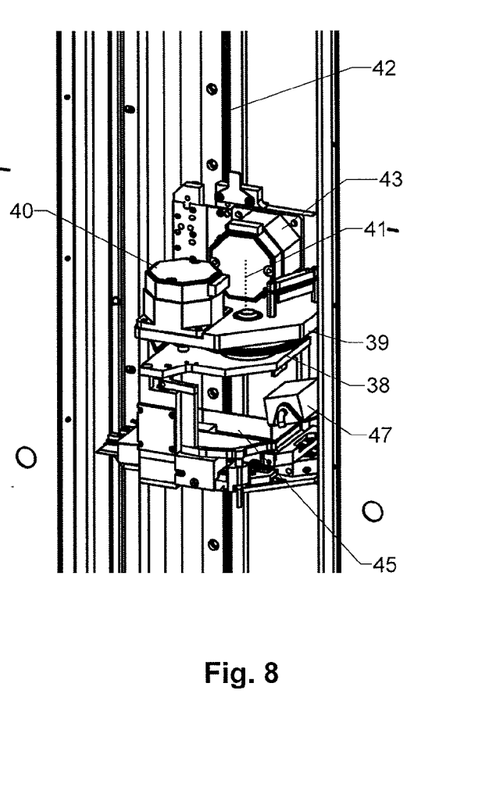
FIG. 8 shows an enlarged view of the transport device of FIG. 7.

As can be seen from FIG. 8, transport device 3 comprises a pivotal and vertically displaceable carriage 38. Carriage 38 is mounted to a carrier 39, with a pivoting motor 40 provided for pivoting carriage 38 in respect to carrier 39 about a vertical pivot axis 41 (the "second axis" in the context of the claims). Carrier 39 is, in its turn, mounted to a vertical guide rail 42 arranged within lock chamber 4. A vertical drive motor 43 is arranged on carriage 38 in order to vertically displace carriage 38 along vertical guide rail 42.

Carriage 38 carries a manipulator 45, whose purpose is to hold the objects to be manipulated. In the shown embodiment, manipulator 45 is formed by a shovel-like table, which can be extended below an object to be picked up and then lifted to engage the object. Other manipulator designs, such as grippers or clamps, are known to the skilled person.

Manipulator 45 has a retracted and an extended position, and it can be extended, in respect to carriage 38, in horizontal direction from its retracted to its extended position in order to pick up or deposit an object. This displacement is achieved by means of a horizontal displacement motor 47.

Pivot axis 41 extends parallel to lock chamber axis 25. However, pivot axis 41 is advantageously located closer to opening 29 than lock chamber axis 25 in order to provide space for thermal insulator 34 and also in order to have manipulator 45 closer to the locations where the objects are stored.

Figure 4:
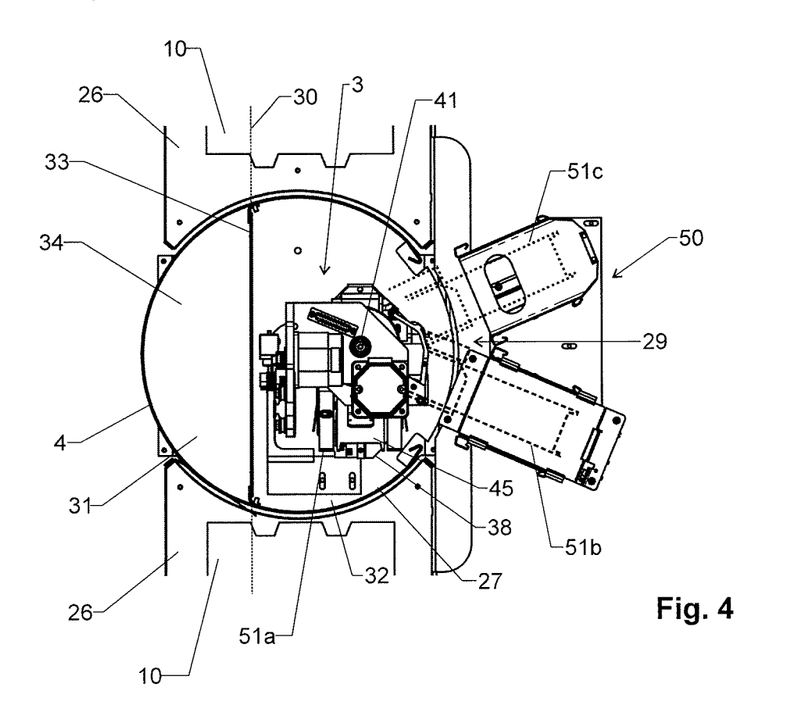
FIG. 4 shows an enlarged view of the device of FIG. 3 depicting the lock chamber and the transport device, with the lock chamber's opening being aligned with the transfer location.

When handling objects in transfer chamber 2, lock chamber 4 is rotated to a first position, as shown in FIG. 4, where opening 29 faces the transfer location 50 in lock chamber 4.

Figure 5:
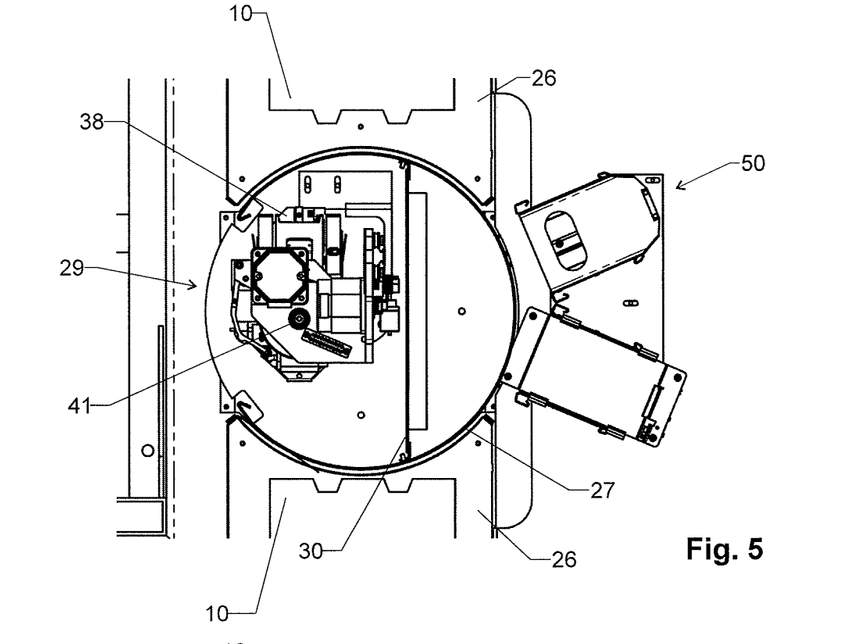
FIG. 5 shows the view of FIG. 4 with the lock chamber's opening being aligned with the storage chamber.

Carriage 38 has at least a first pivotal position 51a, which is shown in solid lines in FIGS. 4 and 5. At this first pivotal position, carriage 38 is located completely within lock chamber 4. It is brought into this first pivotal position 51a when lock chamber 4 is to be rotated.

From its first pivotal position 51a, carriage 38 can be pivoted about pivot axis 41 into at least one second pivotal position (two such pivotal positions 51b, 51c are shown in FIG. 4), where the axis of extension of manipulator 45 aligns with a location of an object to be handled. In this second pivotal position, carriage 38 extends through opening 29, even when it is in its retracted position. In other words, pivoting carriage 38 from its first pivotal position 51a to its at least one second pivotal position 51b, 51c brings manipulator 45 closer to the location of the object to be handled.

In order to take up an object, manipulator 45 is brought into its extended position and inserted below the object, then it moved upwards by a small distance to engage the object, whereupon it can be moved by to its retracted position.

While rotating lock chamber 4 about its lock chamber axis 25, manipulator 45 is in its retracted position and pivoted into its first pivotal position 51a.

Figure 6:
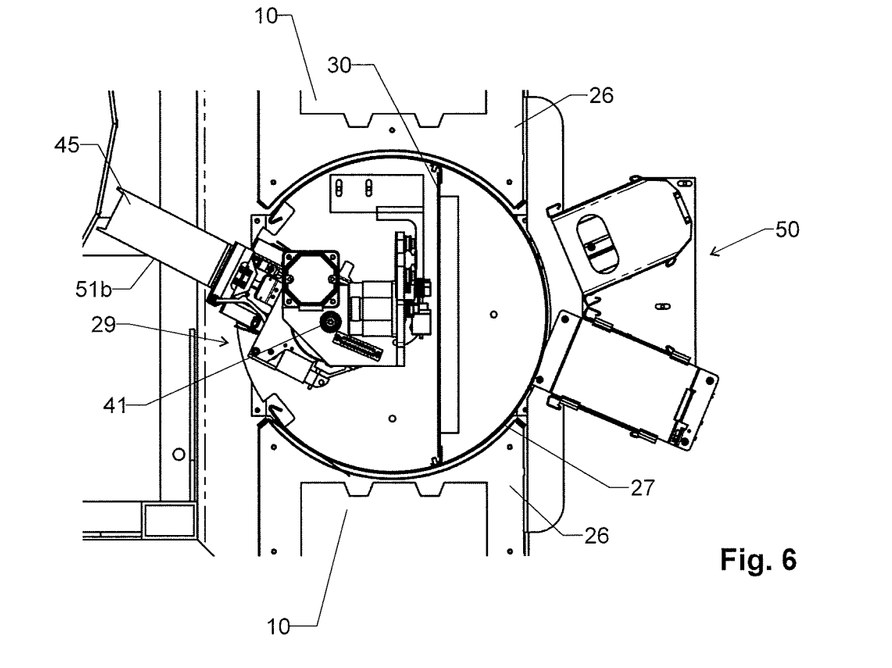
FIG. 6 shows the view of FIG. 5 with the manipulator device in its extended position.

When handling objects in storage chamber 1, lock chamber 4 is rotated to a second rotational position, as shown in FIGS. 5 and 6, where opening 29 faces storage chamber 1. In this case, carriage 38 can again be brought into its second pivotal position 51b, where manipulator 45 can be extended into one of the carousel storage locations 21.

Transfer Chamber:

As mentioned, transfer chamber 2 holds a transfer location 50, where objects to be accessed by transport device 3 are located.

Figure 9:
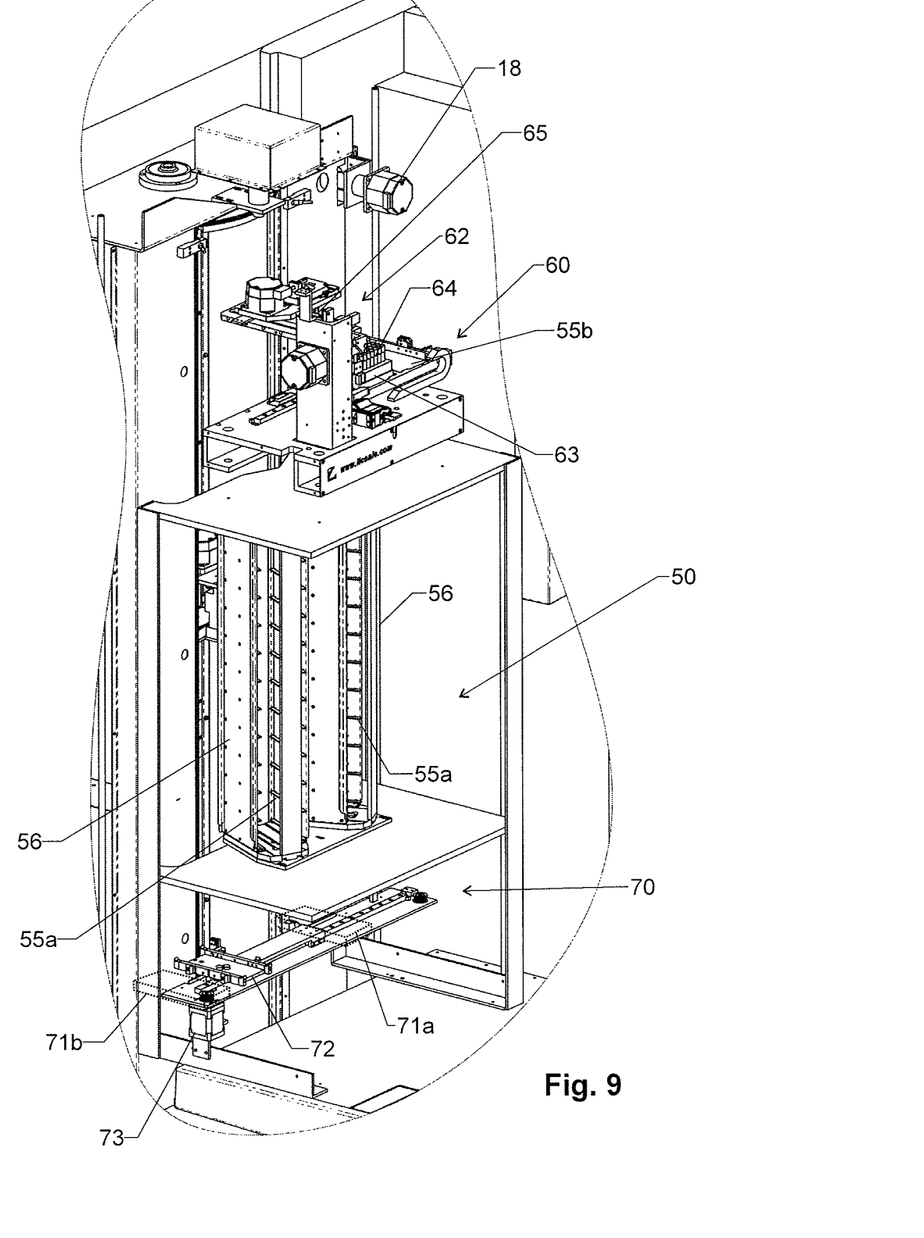
FIG. 9 shows a set of components arranged in the transfer location.
Figure 10:
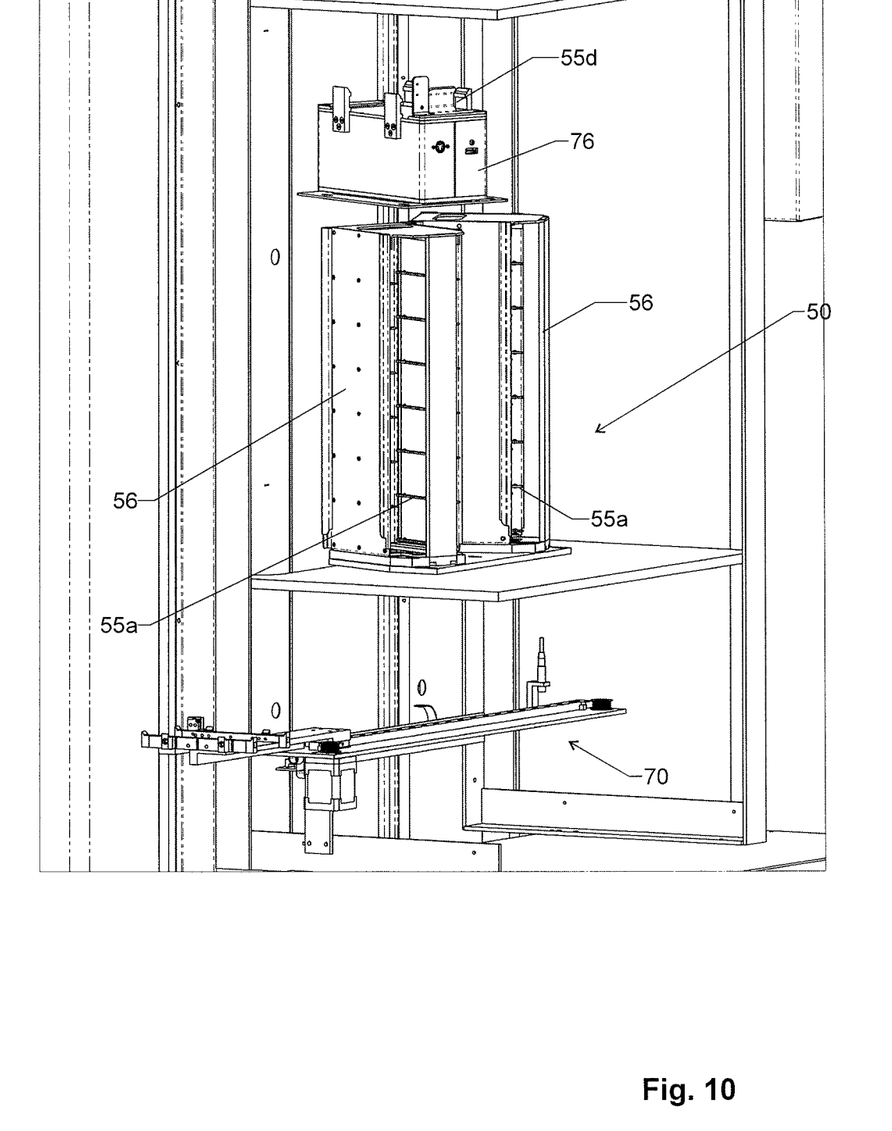
FIG. 10 shows an alternative set of components arranged in the transfer location.

Advantageously, transfer location 50 forms a plurality of locations 55a-55d adapted to receive objects, as shown in FIGS. 9 and 10. Each object storage location 55a-55d is adapted to receive one object.

In the embodiments of FIGS. 9 and 10, two transfer stores 56 are arranged at storage location 50. Each transfer store 56 forms a plurality of transfer storage locations 55a above each other. The transfer stores 56 are arranged side by side at different angular locations in respect to pivot axis 41 of carriage 38 (when lock chamber 3 is in the position where its opening 29 faces transfer location 50 as shown in FIG. 4). Hence, each transfer store 56 can be reached by manipulator 45 by pivoting carriage 38 into two different second pivotal position 51b, 51c (cf. FIG. 4).

In the embodiment of FIG. 9, the present device further comprises an item picker 60 at transfer location 50. Item picker 60 serves to remove individual items from an object or to insert an individual item into an object. This type of functionality is advantageously used when the objects are tube holders, with each object holding a plurality of sample tubes (i.e. items).

Item picker 60 comprises an item picker location 55b for receiving one object from transport device 3. This is e.g. a holder adapted to receive a single plate in SBS format.

Item picker 60 further comprises a picker device 62, which is adapted for removing an individual item from the plurality of items in the object at picker location 55b and/or for adding an individual item to the plurality of items in the object at picker location 55b.

In the embodiment of FIG. 9, item picker 60 comprises an item store 63, which can be used to store individual items 64. A gripper 65 can be displaced along three mutually perpendicular axes in order to reach every item in the object at picker location 55b as well as every item in item store 63 and to move the items between these two positions.

Item picker 60 is arranged vertically above (or below) the storage locations 55a. Carriage 38 of transport device 3 can be vertically displaced and pivoted for being aligned with picker location 55b or one of the storage locations 55a.

In the embodiments of FIGS. 9 and 10, the present device further comprises a transfer device 70 located in transfer chamber 2. Transfer device 70 is adapted and structured to transfer the objects between a first and second object location 71a, 71b (see FIG. 9). For this purpose, it comprises an object holder 72 displaceable along a horizontal guide rail 73 between the object locations 71a, 71b by means of a transfer drive 73 and a drive chain.

First object location 71a forms one of the object locations that can be reached by the manipulator 45 of the transport device. Carriage 38 can be pivoted and vertically displaced for aligning manipulator 45 with first object location 71a. First object location 71a is located below (or above) the transfer storage locations 55a.

Second object location 71b is located at an opening 74 of an exterior housing 80 of the present storage device (see FIG. 2 for opening 74, FIG. 1 for exterior housing 80). From second object location 71b, the object can be accessed by an external robotic system or by a user.

FIG. 10 shows yet another component that can be arranged at transfer location 50, namely an optical scanner 76. It forms a scanner location 55d for receiving an object, which can be reached by manipulator 45. For this purpose, carriage 38 can be vertically displaced and pivoted to align manipulator 45 with scanner location 55d.

Scanner 76 is used to scan markings on the objects and/or on items held by the objects.

Exterior Design:

As already mentioned and as shown in FIG. 1, the present storage device comprises an exterior housing 80 enclosing storage chamber 1 as well as transfer chamber 2.

A first door 81 is provided at the wall of storage chamber 1 and provides access to the interior of storage chamber 1. This door remains typically closed when the storage device is in use, but it may be opened for major service and maintenance.

A second door 82 is provided at the wall of transfer chamber 2 and provides user access to the components within access chamber 2.

A third door 83, which is smaller than second door 82, is also provided at the wall of transfer chamber 2 to cover opening 74, through which objects can be accessed at second object location 71b (see FIG. 9).

Refrigerator Device:

As mentioned, the present storage device comprises a refrigerator device 5 for maintaining the temperatures within storage chamber 1 and transfer chamber 2.

Figure 12:
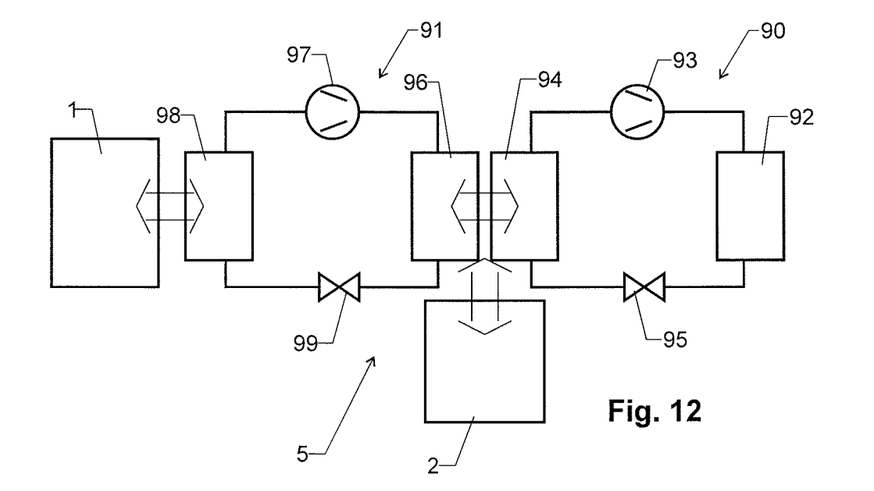

An advantageous embodiment of such a device is shown in FIG. 12. It comprises a first heat pump 90 and a second heat pump 91. First heat pump 90 comprises a condenser 92, a compressor 93, an evaporator 94 and an expansion valve 95. Compressor 93 pumps a fluid through condenser 92, expansion valve 95 and evaporator 94 in order to transfer heat from evaporator 94 to condenser 92 in a generally known manner. Similarly, second heat pump 91 comprises a condenser 96, a compressor 97, an evaporator 98 and an expansion valve 99. Compressor 97 also pumps a fluid through condenser 96, expansion valve 99 and evaporator 98 in order to transfer heat from evaporator 98 to condenser 96.

First heat pump 90 is structured and adapted to pump heat from transfer chamber 2 to the environment. For this purpose, evaporator 94 is in thermal contact with transfer chamber 2 and condenser 92 is in thermal contact with the environment.

Second heat pump 91 is structured and adapted to pump heat from storage chamber 1 to evaporator 94 of first heat pump 90. In other words, the heat pumps 90, 91 are thermally arranged in series. For this purpose, evaporator 98 of second heat pump 91 is in thermal contact with storage chamber 1, condenser 96 of second heat pump 91 is in thermal contact with evaporator 94 of first heat pump 90, and evaporator 98 of second heat pump is in thermal contact with storage chamber 1.

This design with two heat pumps arranged "in series" and the first heat pump also being used to cool transfer chamber 2 provides a high level of efficiency.

Notes:

In the embodiment shown above, storage chamber 1 holds a single carousel and has substantially quadratic footprint. Alternatively, storage chamber 1 can be of rectangular footprint and hold two carousels side-by-side, or the carousel can be replaced with some other type of apparatus suitable for storing the objects.

In the example above, carriage 38 is pivotal as well as vertically displaceable. However, depending on its application, it could also only be pivotal or only be vertically displaceable.

Advantageously, transfer location 50 is located in transfer chamber 2. This allows to maintain transfer location 50 at a temperature below 0° C. and at low humidity, thereby reducing the amount of moisture passing into storage chamber 1 during operation of transport device 3. However, in an alternative embodiment, transfer chamber 2 can be dispensed with—in this case, transfer location 50 is located e.g. outside the outer housing of the storage device.

While there are shown and described presently preferred embodiments of the invention, it is to be distinctly understood that the invention is not limited thereto but may be otherwise variously embodied and practiced within the scope of the following claims.

The invention claimed is:

1. A low-temperature storage device for storing a plurality of objects, comprising
   a storage chamber for receiving said objects,
   a refrigerator device adapted and structured to cool said storage chamber to a storage temperature below 0° C., in particular below −20° C.,
   an insulating wall enclosing said storage chamber,
   a transfer location arranged outside said storage chamber,
   a lock chamber arranged in said insulating wall, wherein said lock chamber comprises a cylindrical housing and an opening arranged in said cylindrical housing, and wherein said lock chamber is rotatable about a first axis for selectively orienting said opening towards said storage chamber or said transfer location,
   an automatic transport device arranged in said lock chamber, wherein said transport device comprises
   a) a carriage pivotal, relatively to said lock chamber, about a second axis and/or displaceable, relatively to said lock chamber, along the second axis, wherein said second axis is parallel to said first axis,
   b) a manipulator arranged on said carriage and extendible from a retracted position in a direction perpendicular to said second axis into an extended position, and
   wherein said transport device is adapted to transport objects between said storage chamber and said transfer location by means of said manipulator.

2. The device of claim 1 wherein said first and said second axes are vertical.

3. The device of claim 1 wherein said second axis is closer to said opening than said first axis.

4. The device of claim 1 wherein said transport device is pivotal about said second axis and displaceable along the second axis.

5. The device of claim 1 further comprising, at said transfer location, a plurality of transfer storage locations, with each transfer storage location adapted to receive one of said objects, wherein said carriage is pivotal about and/or displaceable along said second axis to be aligned with each of said transfer storage locations.

6. The device of claim 5 comprising at least two transfer stores, wherein each transfer store forms a plurality of said transfer storage locations above each other, wherein said transfer stores are arranged beside each other at different angular locations in respect to said second axis.

7. The device of claim 1 further comprising, at said transfer location, an item picker, which item picker comprises an item picker location for receiving an object and a picker device structured and adapted for removing an individual item from a plurality of items in said object at said picker location and/or for adding an individual item to a plurality of items in said object at said picker location, wherein said carriage is pivotal about and/or displaceable along said second axis to be aligned with said picker location.

8. The device of claim 7 further comprising, at said transfer location, a plurality of transfer storage locations, with each transfer storage location adapted to receive one of said objects, wherein said carriage is pivotal about and/or displaceable along said second axis to be aligned with each of said transfer storage locations, wherein said transfer storage locations are arranged above or below said item picker.

9. The device of claim 1 further comprising a transfer chamber receiving said transfer location, wherein said refrigerator device is adapted and structured to cool said transfer chamber to a transfer temperature below 0° C., but above said storage temperature.

10. The device of claim 9 wherein said refrigerator device comprises a first heat pump and a second heat pump, with said first heat pump being structured and adapted to pump heat from said transfer chamber to an environment and said second heat pump being structured and adapted to pump heat from said storage chamber to an evaporator of said first heat pump.

11. The device of claim 9 further comprising, in said transfer chamber, a transfer device structured and adapted to transfer objects between a first and second object location, wherein said carriage is pivotal about and/or displaceable along said second axis to be aligned with said first object location and to reach an object in said first object location, and wherein said second object location is located at an opening of an exterior housing of said low-temperature storage device.

12. The device of claim 11 further comprising, at said transfer location, a plurality of transfer storage locations, with each transfer storage location adapted to receive one of said objects, wherein said carriage is pivotal about and/or displaceable along said second axis to be aligned with each of said transfer storage locations, wherein said transfer storage locations are arranged above or below said first object location.

13. The device of claim 1 further comprising, at said transfer location, a scanner structured and adapted to scan markings on said objects or on items held by said objects, wherein said scanner forms a scanner location, and wherein said carriage is pivotal about and/or displaceable along said second axis to be aligned with said scanner location.

14. The device of claim 1 further comprising a carousel arranged in said storage chamber, wherein said carousel is rotatable about a third axis parallel to said first axis, and wherein said carousel forms a plurality of carousel storage locations, each for receiving one object.

15. The device of claim 14 wherein said carousel is suspended from a rotational bearing arranged at the top or above said carousel.

16. The device of claim 14 further comprising a carousel drive for rotating said carousel about said third axis, wherein said carousel drive comprises a carousel motor arranged outside said storage chamber and a shaft driven by said carousel motor and extending into said storage chamber.

17. The device of claim 16 wherein said shaft extends perpendicularly to said third axis and wherein said device further comprises an angular gear connecting said shaft to said carousel.

18. The device of claim 16 further comprising a transfer chamber receiving said transfer location, wherein said refrigerator device is adapted and structured to cool said transfer chamber to a transfer temperature below 0° C., but above said storage temperature, wherein said carousel motor is arranged in said transfer chamber.

19. The device of claim 1 wherein said lock chamber further comprises a thermal insulator arranged within said cylindrical housing, wherein a thickness of said thermal insulator in a direction radially in respect to said second axis is at a maximum at a location opposite said opening.

20. The device of claim 19 wherein said thickness at said maximum is at least 50% of a radius of said cylindrical housing.

21. The device of claim 1 wherein said opening extends from a top of said lock chamber to a bottom of said lock chamber.

22. The device of claim 1 wherein said carriage has a first pivotal position where it is, in its retracted position, located completely within said lock chamber and from where it is pivotal into at least a second pivotal position, where it extends, in its retracted position, through said opening.

23. The device of claim 22 wherein said carriage is pivotal into at least two second pivotal positions at different angular locations, and wherein said device further comprises at least two locations for receiving objects at said different angular locations.

* * * * *